United States Patent [19]

Lepley

[11] Patent Number: 5,271,416
[45] Date of Patent: Dec. 21, 1993

[54] EXERCISE PLATFORM FOR PHYSIOLOGICAL TESTING

[75] Inventor: Jan C. Lepley, Eagle River, Ala.

[73] Assignee: Alaska Research & Development, Inc., Anchorage, Ala.

[21] Appl. No.: 33,145

[22] Filed: Mar. 16, 1993

Related U.S. Application Data

[63] Continuation-in-part of Ser. No. 760,762, Sep. 16, 1991, abandoned.

[51] Int. Cl.$^5$ ............................................. A61B 5/103
[52] U.S. Cl. ................................. 128/782; 128/25 R; 482/5; 482/120
[58] Field of Search ............... 128/779, 781, 782, 774, 128/25 R, 25 B; 482/4, 5, 8, 9, 72, 91, 114, 115, 120, 901; 364/413.01, 413.02; 73/379

[56] References Cited

U.S. PATENT DOCUMENTS

| | | | |
|---|---|---|---|
| 4,122,840 | 10/1978 | Tsuchiya et al. | 128/779 |
| 4,337,050 | 6/1982 | Engalitcheff, Jr. | 434/260 |
| 4,471,957 | 9/1984 | Engalitcheff, Jr. | 482/5 |
| 4,475,408 | 10/1984 | Browning | 73/862.12 |
| 4,628,910 | 12/1986 | Krukowski | 128/25 R |
| 4,637,607 | 1/1987 | McArthur | 482/115 |
| 4,768,783 | 9/1988 | Engalitcheff, Jr. | 482/139 |
| 4,912,638 | 3/1990 | Pratt, Jr. | 364/413.02 |
| 5,070,863 | 12/1991 | McArthur et al. | 128/25 R |

OTHER PUBLICATIONS

Chaffin et al., "Intradiscal Pressure Measurement" Bioinstrumentation for Occupational Biomechanics, pp. 134, 135, 210 and 211, date unknown.

Primary Examiner—Stephen C. Pellegrino
Assistant Examiner—Guy V. Tucker
Attorney, Agent, or Firm—Arnold, White & Durkee

[57] ABSTRACT

A device is disclosed for performing a quantitative analysis of a patient during exercise against isometric, isokinetic, or isoinertial resistance, in order to construct a detailed musculoskeletal model of a human subject. To use the device, the subject grasps a handle which is attached to a length of cable, wound upon a cable spool. Adjustable braking means attached to the cable spool supplies isometric, isokinetic, or isoinertial resistance against unwinding of the cable in order to simulate selected lifting motions. Sensing devices detect the longitudinal and lateral angles at which the patient is pulling the cable. A torsion spring is attached to the cable spool for rewinding the cable. In the preferred version, force sensors are attached to an upper surface of the platform to detect the manner in which the subject's weight is distributed between the anterior and posterior regions of the subject's feet, as well as between the subject's right and left feet. In an alternative embodiment, one or more cameras can be placed at selected positions relative to the lifting platform in order to monitor different aspects of the patient's body during lifting activity. A computing station is attached to the sensors available in the particular embodiment being utilized, including the cameras if present, and functions to analyze data received therefrom in order to create a biomedical model representative of the patent for use in evaluation. The computing station can also be adapted to accept input from a goniometer in order to perform analysis of the patient's lumbar spine.

15 Claims, 5 Drawing Sheets

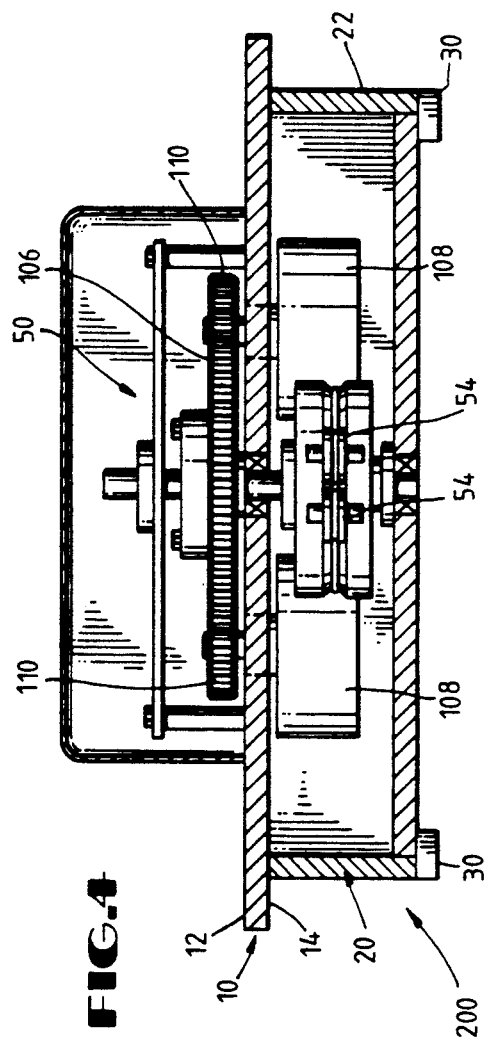
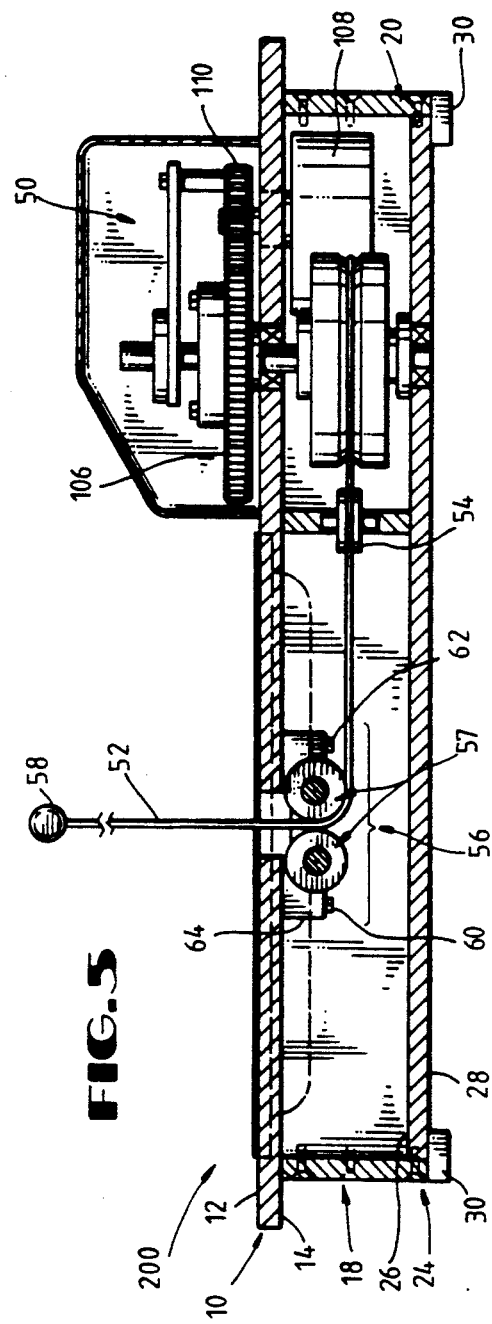

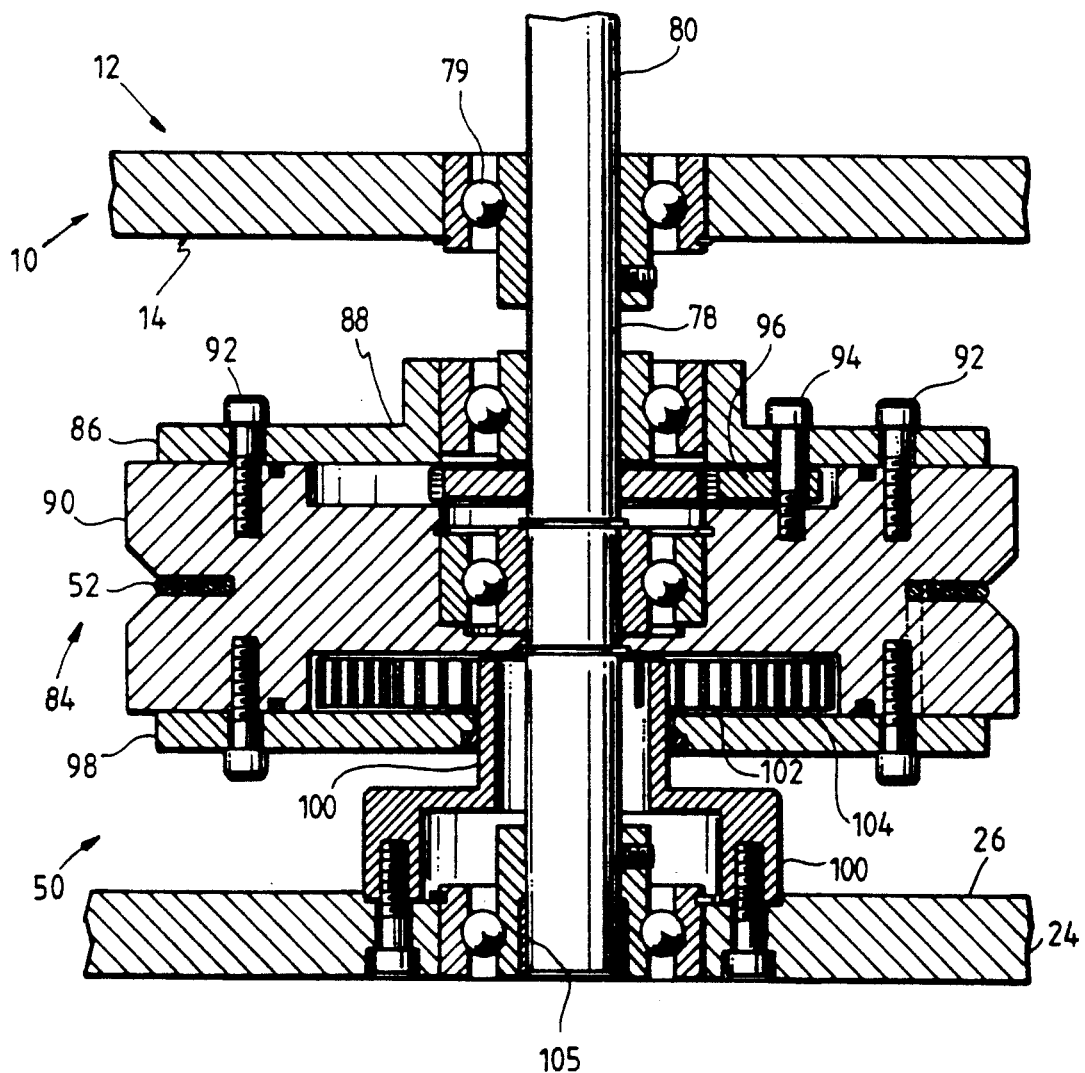

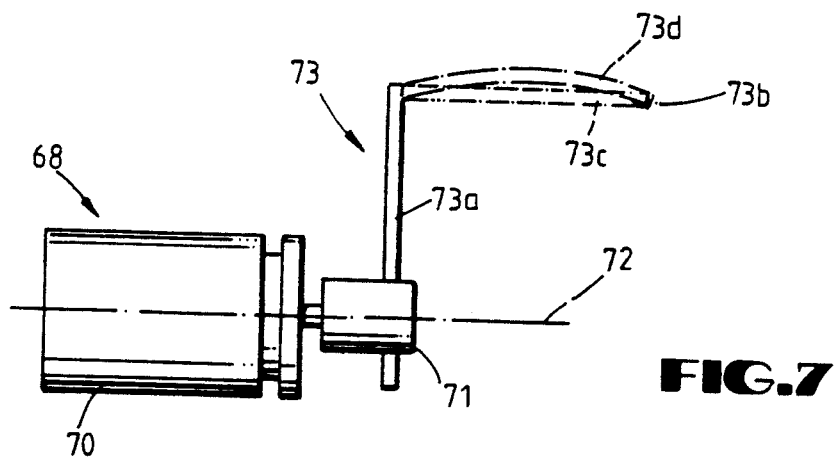
FIG. 7
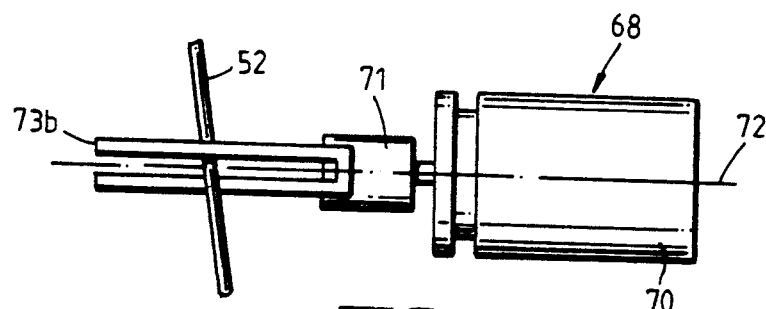
FIG. 8
FIG. 10
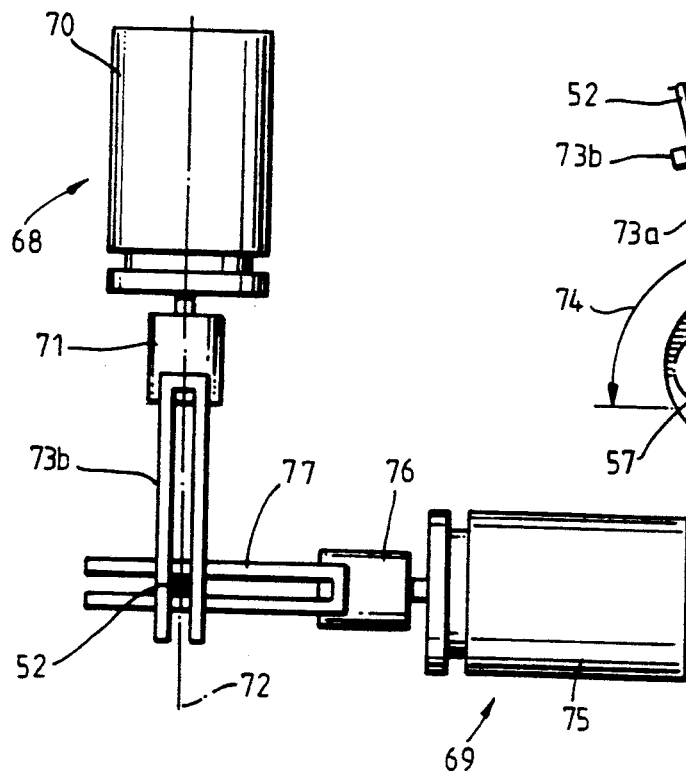
FIG. 9
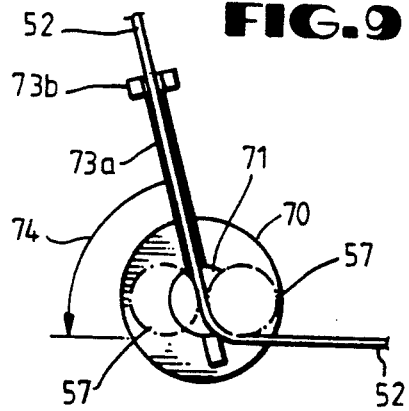

EXERCISE PLATFORM FOR PHYSIOLOGICAL TESTING

CROSS-REFERENCE TO RELATED APPLICATIONS

The present application is a continuation-in-part of U.S. patent application Ser. No. 07/760,762, entitled "Exercise Platform for Physiological Testing," filed Sep. 16, 1991 in the name of Jan Chelsea Lepley, the sole present inventor, now abandoned.

BACKGROUND OF INVENTION

1. Field of the Invention

The present invention relates generally to diagnostic systems for exercising and evaluating characteristics and capacity of the human body during lifting. More particularly, the invention relates to an improved machine, system and method for determining characteristics of a patient's body during lifting exercises.

2. Description of Related Technology

In the field of exercise physiology, one type of resistance to muscular exertion is known as isometric resistance. Isometric resistance is designed to preclude movement at any level of exertion by the user. More specifically, it is the attempted motion of a stationary object where the length of the muscle fibers involved in the exercise does not change.

Isometric resistance has been utilized in the past to analyze the human body during lifting operations. Examples of currently available products that utilize isometric resistance are the ISTU manufactured by Ergometrics Inc. and the Arcon ST by Applies Rehabilitation Concepts. While these systems have been useful for some purposes, they suffer a number of disadvantages.

In particular, diagnostic systems which employ isometric resistance are unable to evaluate certain types of injuries, such as the injuries where a patient only experiences pain during actual movement of an affected body part. Moreover, since isometric systems are static, they are unable to accurately project a patient's actual dynamic lifting capacity. It is well known in the art that the strength of a particular body part varies depending upon the positioning of that body part. Testing systems that employ isometric resistance are typically limited to one exercise position. Therefore, these systems are insufficient to accurately determine a patient's dynamic lifting capacity. Furthermore, since isometric systems do not involve any muscular movement of the patient, these systems lack the capacity to accurately evaluate muscular endurance.

An alternate means for resistance muscular exertion, in contrast to isometric resistance, is dynamic resistance. Dynamic resistance is resistance permitting actual movement of an object by a person exerting force against it. Dynamic resistance involves the shortening and lengthening of the person's muscle fibers. Today it is generally understood that there are three basic types of dynamic resistance; isotonic, isokinetic and isodynamic.

Isotonic resistance involves the use of gravity or the simulation of gravity to resist muscular exertion. Some examples of exercise equipment utilizing isotonic resistance include free weights such as barbells, as well as Universal brand weight lifting machines. While the forces of gravity remain constant, the resistance to motions, such as lifting, varies during the movement because of the skeletal angle changes.

Muscle movement against isotonic resistance occurs in two categories. First, the contractile phase involves shortening the muscle fibers while the weight is moved against gravity, or in other words "lifting" the weight. Second, the eccentric phase refers to motion wherein the muscle fibers are lengthened while the weight is moved in the same direction as the force of gravity, or in other words "lowering" the weight.

Exercise machines that provide isotonic resistance by using resistance other than weights are well known in the art. For example, a hydraulic source used to supply isotonic resistance is disclosed in U.S. Pat. No. 4,865,315 to Paterson et al., entitled "Dedicated Microprocessor Controlled Exercise Resistance Machine." In addition to hydraulic sources, isotonic resistance has been provided by pneumatic sources, as illustrated in U.S. Pat. No. 4,257,593 to Keiser, entitled "Pneumatic Exercising Device".

Exercise apparatuses that provide isotonic resistance have been adequate for some purposes. For example, machines that provide isotonic resistance are able to duplicate the resistance encountered when lifting a physical object against gravity. Therefore, these systems can resemble "real life" situations.

Isokinetic resistance, as now understood, restricts motion to approximately constant velocity, irrespective of the amount of force applied by the patient. Exercise machines that provide isokinetic resistance are well known in the art, and have used a number of different means for resistance. For example, systems are known that provide adjustable isokinetic resistance with mechanical or electric braking devices. Additionally, hydraulic sources have been used in the provision of isokinetic resistance. An example of an exercise machine that provides isokinetic resistance is the Cybex Liftask brand system, which is sold by Lumex Industries. Another example of an apparatus that provides isokinetic resistance to exercise is the Biodex dynamometer sold by Biodex Corp. of Shirely, N.Y. The biodex dynamometer adapts to provide isokinetic resistance for use in quantifying flexion and extension movements of a patient's lower spine and other rotational movements about an isolated single axis such as knee flexion/extension.

Exercise machines that provide isokinetic resistance have been sufficient for some purposes. Specifically, users of exercise or quantitative machines that utilize isokinetic resistance have enjoyed a substantial degree of safety, since they are free to exert as much or as little force against the resistance as they wish without altering their rate of motion. Isodynamic resistance, or alternately, isoinertial resistance, exerts an approximately constant force during exercise, thereby allowing for changes in acceleration and velocity of motion in proportion to the force applied by the user. Isodynamic devices previously were also referred to as "isokinetic" and a distinctions between the two has only recently been recognized by the industry.

Exercise machines providing isodynamic resistance are known in the art. For example, U.S. Pat. No. 4,733,859 to Kock et al., entitled "Exercise Apparatus" utilizes isodynamic resistance in conjunction with neck or foot exercise. Isodynamic resistance has been useful in a number of applications, and is considered reasonably similar to "real world" lifting conditions because this resistance allows changes in movement velocity in proportion to changes in muscular force. Isodynamic systems have been used to obtain measurements such as the velocity of the weight lifted and the torque on an exercising joint, in order to evaluate a patient's level of impairment or to monitor a patient's recovery.

Exercise and quantitative machines for lifting movements utilizing isometric, isokinetic, or isotonic resistance modes have been used with some success, but the measurements they provide are not as versatile or comprehensive as might be desired in some contexts. In particular, these machines lack versatility if they only offer a single mode of resistance or limited options. Thus, the evaluations performed with these machines are not as useful as needed for some applications.

There are presently a number of machines that can furnish multiple modes of exercise resistance. Two examples of machines that facilitate neck exercise against dynamic or isometric resistance are U.S. Pat. No. 4,768,779 to Oehman, Jr. et al., entitled "Back Exercise Apparatus with a Neck Exercise Attachment" and U.S. Pat. No. 4,893,808 to McIntyre et al., entitled "Exercise Apparatus For the Neck" are examples. The Oehman, Jr. et al. and McIntyre machines also supply data in order to facilitate the computerized determination of parameters associated with the exercise, such as angular position, velocity, and torque. In addition, there are machines which apparently do provide multiple modes of resistance, such as LIDO Lift by Loredan, Kin-Com by Chattex, and Isonertial Lift Device by Baltimore Therapeutics, but none of those devices offer the potential for assessing weight distribution during lifting.

In addition, Cybex, a division of Lumex Industries, makes the Liftask device, which is a dynamic cable-actuated lifting platform that is based on isokinetic resistance. While the Lifttask device does allow the torque curve for the entire multi-joint lifting motion to be measured, the unit will not provide isoinertial resistance and therefore any potential information associated with velocity and acceleration measures against a constant force cannot be examined. It is known that velocity and acceleration measures are sensitive indicators of consistent effort, which is important is ascertaining malingering, one goal of the claimed invention.

Although the above-described systems have often been satisfactory for their intended purposes, they all share a number of disadvantages when considered for some uses. In particular, none of these machines accurately simulate occupational conditions where various objects are lifted in an unconstrained environment. Accordingly, a system is needed in order to provide data relating to the musculoskeletal activity of a patient during weight lifting exercises similar to the lifting of objects. Additionally, it would be beneficial to rehabilitation and evaluation to have a system that provides a comprehensive report of the velocity, magnitude, a real-time position of the weight lifted during such exercises.

Another limitation of present exercise and diagnostic systems is that they do not provide any information relating to an exercising patient's weight and force distributions during lifting-type exercise. In U.S. Pat. No. 4,738,269 to Nashner, entitled "Apparatus and Method for Sensory Integration and Muscular Coordination Analysis", an irregularly moving rectangular platform having a total of four pressure sensors positioned with two independently connected under each foot in conjunction with various sensory inputs is used to test a patient's ability to maintain his/her equilibrium. Systems such as that of Nashner, although adequate for their intended purposes, lack usefulness in qualifying a patient's weight distribution placed on his/her feed during lifting exercise. Such information would be valuable in determining musculoskeletal strategies for the patient to maintain proper balance, prevent injuries, and minimize the pain caused by existing physiological problems. Therefore, it would be beneficial to have a system, such as a weight lifting platform, capable of supplying detailed information about the patient's weight distribution during lifting exercises.

Furthermore, feedback concerning the musculoskeletal condition of a patient during lifting exercises would be valuable for conducting calculations such as joint torques and spinal compressions during movement. However, the ability of the present technology to provide such information is limited. Therefore, it would be of distinct value to have a system that provides a comprehensive musculoskeletal analysis of the user during lifting exercising, so that condition such joint stress, spinal compression, and the like can be evaluated.

It would also be advantageous to have an evaluation system that selectively provides isometric, isotonic, isokinetic, or isodynamic resistance, and additionally supplies sufficient data for analysis of muscular endurance, maximal dynamic lifting capacity, and weight distribution. Also, it would be beneficial to help evaluate injuries related to specific conditions and ranges of movement.

SUMMARY OF INVENTION

A lifting station includes footplates resting on force sensors that produce a signal or a detectable change proportional to the force applied. The lifting station also includes a cable assembly for dispensing, rewinding and storing a cable having a handle connected at one end. To use the lifting station, the user stands on the footplates, grasps the handle, and lifts or pulls it. During this lifting action, feedback resistance to the user's pull on the cable is supplied by selectively braking the dispensing of the cable. This resistance causes a change in the strain on the body which in turn causes a change on the forces exerted by the feet on each footplate.

While the user lifts, the force sensors under each footplate quantify the force that they experience. Additional sensors are employed to the quantify the lateral angle at which the cable is dispensed, the longitudinal angle at which the cable is dispensed, length of cable dispensed, and the velocity at which the cable is dispensed and rewound. This data is used to generate an output relative to the lifting strategy and force of the user.

BRIEF DESCRIPTION OF THE DRAWINGS

With these and other objects in view, as will hereinafter more fully appear, and which will be more particularly pointed out in the appended claims, reference is now made to the following description taken in connection with the accompanying drawings in which:

FIG. 4 is a front view cut-away drawing of the lifting station of the present invention showing more clearly the cable assembly and braking mechanisms;

FIG. 5 is a side view cut-away drawing of the lifting station of the present invention showing more clearly the cable assembly and cable guide mechanisms;

FIG. 6 is a more detailed cut-away drawing of the cable assembly;

FIG. 7 is a side view of a first angle sensor 68 of the invention;

FIG. 8 is a top plan view of the first angle sensor 68 of the invention;

FIG. 9 is a side view of the first angle sensor 68 in relation to a second roller 57, in accordance with the invention; and FIG. 10 is a top view of the first angle sensor 68 and a second angle sensor 69 of the invention.

DESCRIPTION OF PREFERRED EMBODIMENT

Figure 1:
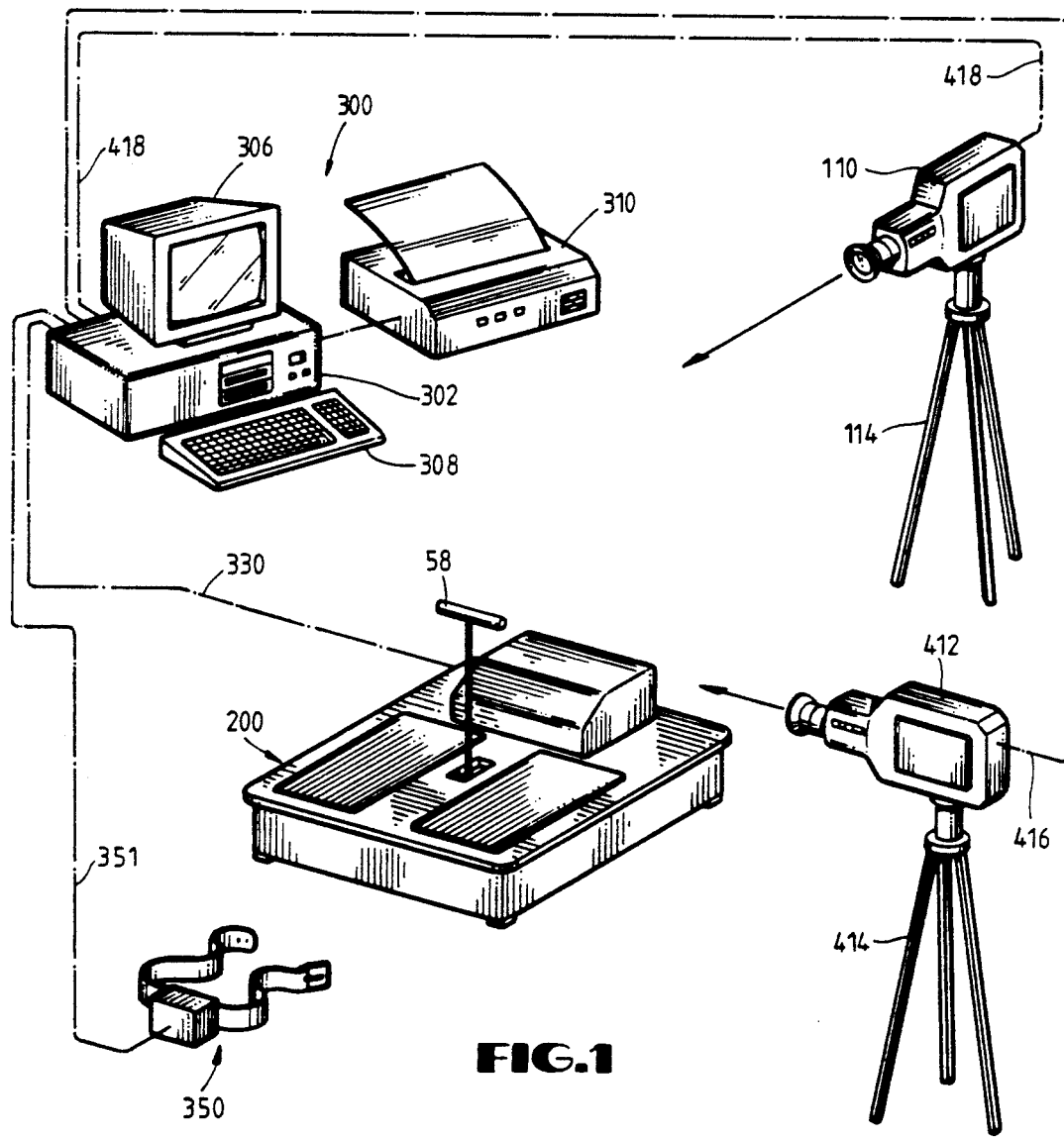
FIG. 1 is a drawing of the overall hardware and interconnections of the present invention.

Referring now to the drawings, a preferred embodiment of the invention will be described. The present invention generally provides an improved system and method for evaluating conditions of the human body during lifting exercises. More specifically, the preferred embodiment comprises a system for constructing a detailed biomedical model of a patient by determining various characteristics of a patient while the patient exercises against selected isometric, isokinetic, or isodynamic resistance.

The principal components of the system of the preferred embodiment include a lifting station 200 (FIG. 2-5) and a computing station 300 (FIG. 1). Referring to FIGS. 2-5, the lifting station 200 is constructed of an upper platform 10, having an upper surface 12 and a lower surface 14. The lower surface 14 is attached to vertical support members 16, 18, 20, and 22. The vertical support members 16, 18, 20, and 22 are additionally connected to a lower platform 24 (FIG. 5), having an upper surface 26. The lower platform 24 additionally has a lower surface 28, to which base members 30 are attached.

Figure 2:
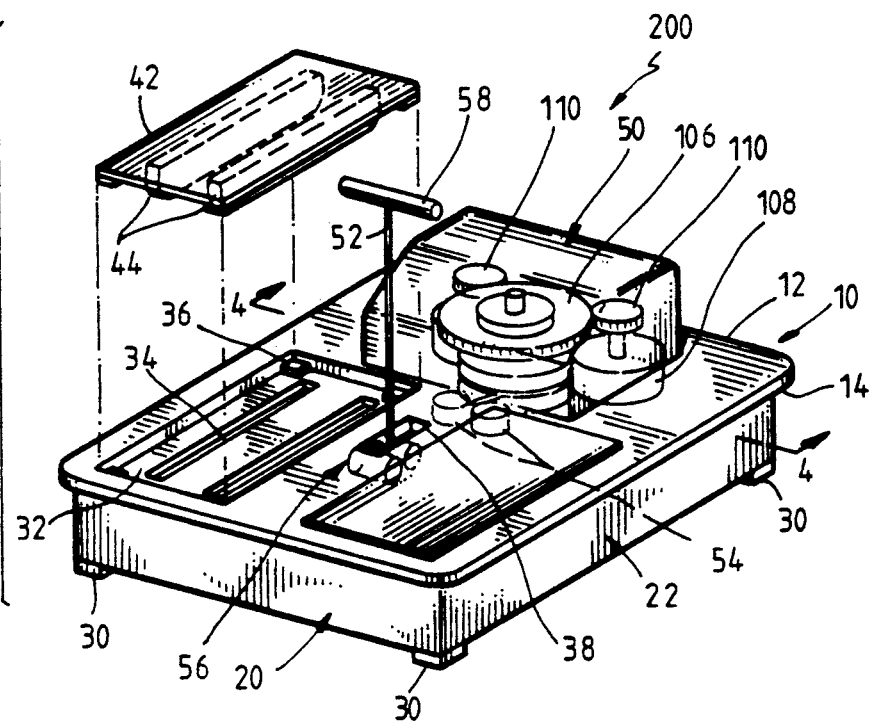
FIG. 2 is an isometric drawing of the lifting station of the present invention.
Figure 3:
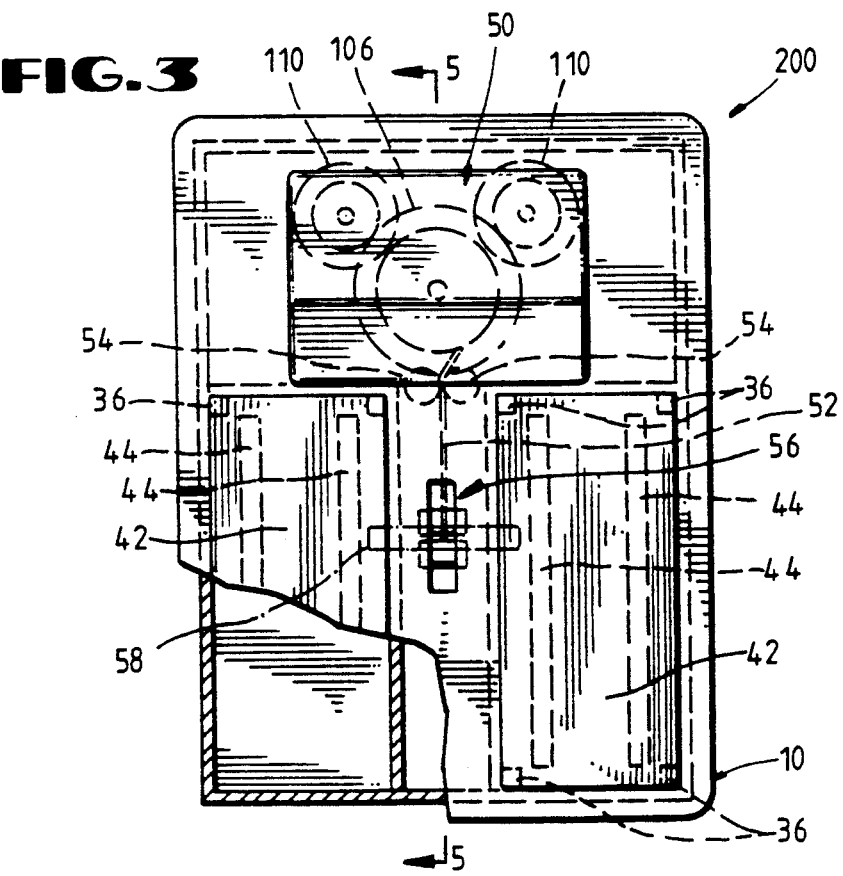
FIG. 3 is a partially cut-away top view drawing of the lifting station of the present invention.

Upper platform 10 has two recessed regions 32 (FIG. 2). In the preferred embodiment, the upper platform 10 is a ⅜" thick sheet of aluminum and the recessed regions 30 are ⅜" inch deep. Truss slots 34 are included in each recessed region 30. At each corner of the recessed regions 30, a force sensor 36 is placed. Each force sensor 36 is connected to a signal wire (not shown) which passes through holes (not shown) drilled though the recessed regions 30 of the upper platform 10. Between the two recessed regions 30, is a cable slot 38, through which a cable 52 can be dispensed from a cable assembly 50 mounted elsewhere in the lifting station 200.

A footplate 42 nestles in each recessed region 30. In the preferred embodiment, each footplate 42 is made of ⅜" thick aluminum. Footplate trusses 44 are fastened to the lower surface of each footplate 42 and fit in truss slots 34 in the recessed region 30.

The weight of the user, together with any strain the user is undergoing from exercising, is transmitted through the user's feet to the footplates 42 and in turn to the forces sensors 36. During exercise, the force sensors 36 are positioned between the footplate 42 and the upper surface of the recessed region 30 in the upper plateform 10. It can be understood that any means of converting pressure or force into an electrical signal could be employed in the lifting station. In the preferred embodiment, force sensing resistors (not shown) are used for the force sensors 36.

It has been learned that the force sensing resistors, and in particular their elastic recovery, are sensitive to the way in which the force exerted upon them. To obtain a more reliable and consistent measurement, it has been found advantageous to insert a force sensor pad (not shown) between a footplate 42 and the force sensing resistor. It has also been learned that accuracy and consistency can vary significantly when different materials are used for the force sensor pad. A metal pad adversely affects accuracy by preventing an even distribution across the force sensing resistor. A rubber foam pad adversely affects consistency, because the resiliency of the foam causes it to rebound slowly from an exertion of force and, if during that recovery period, a new force is put on the rubber pad, the output of the force sensing resistor will be different that if the rubber pad and been fully restored to its original position.

In the preferred embodiment, the applicant used Poron ® which is made by the G. F. Cole Co. and supplied with the force sensing resistors by the resistor manufacturer, Interlink Electronics, For convenience, the force sensor pads may be attached by gluing or other suitable means to the lower surface of footplates 42, and the force sensing resistors may be glued by a thin layer of adhesive to the upper surface of the recessed region 30 of the upper plate 10.

It has also been learned that the footplates 42 in the preferred embodiment, made of aluminum, exhibit some degree of bending when the user stands on them. This bending may cause distortion of the force exerted on the force sensors 36. The footplate trusses 44 are added to effectively reduce distortions from bending. It is preferable that the footplates 42, whether of aluminum or other suitable material, be as entirely rigid and free from both longitudinal and lateral flexion as possible so as to minimize or, optimally, prevent distortion and therefore biased compression of the force sensor 36.

Referring to FIGS. 2-6, a cable assembly 50 is contained in the lifting station near the front. The cable 52 from the cable assembly 50 passes through first cable guide rollers 54 and then to a cable guide assembly 56, which includes a pair of second cable guide rollers 57. The cable passes through the second cable guide rollers 57 and upward through the cable slot 38 of the upper platform 10. A handle 58 is connected to the cable 52 above the upper surface 12 of the upper platform 10. Thus, a user in operation grasps the handle 58 and lifts upwards, which pulls cable 52 from the cable assembly 50 past the cable guide rollers 54 and the cable guide assembly 56. The second rollers 57 guide the cable about an approximate 90° turn to the essentially vertical direction of pull or lift by the user. The second rollers 57 are fastened to a cable guide bracket 64, which is affixed to the platform 10 by cable guide mounts 60 and 62.

A more detailed view of the cable assembly 50 is shown in FIG. 6. An axle 78 is mounted vertically within the lifting station 200. An upper end 80 of the axle 78 passes through a hole in the upper platform 10, and is rotatably mounted within bearings 79 attached to the lower surface 14 of upper platform 10. A pulley assembly 84 is mounted about the axle 78. The pulley assembly 84 includes a first pulley plate 86 mounted on bearings so as to be freely rotatable about axle 78. A ratchet 88 is mounted adjacent to the first pulley plate 86. Ratchet 88 is fixedly mounted about axle 78. A cable spool 90 is mounted adjacent to the ratchet 88, and is mounted on bearings so as to be freely rotatable about the axis 78. The first pulley plate 86 and cable spool 90 are fixed to each other by bolts 92. A bolt 94 assists in positioning the first pulley plate 86 and the cable spool 90 in fixed relation to each other. Additionally, the bolt 94 secures a ratchet pawl 96 between the first pulley plate 86 and the cable spool 90, such that the ratchet pawl 96 is operative contact with the ratchet 88.

The ratchet 88 and the ratchet pawl 96 are arranged so as to engage when the cable spool 90 is turned in a direction that would cause the cable 52 to unwind off the cable spool 90. The ratchet 88 and ratchet pawl 96 are arranged to not engage when the cable spool 90 turns in the opposite direction. Since the ratchet 88 is fixed to the axle 78 and the cable spool 90 is freely rotatable about the axle 78, the ratchet arrangement operates such that when cable 52 is pulled from the cable spool 90, a torque is imparted to the axle 78. When the cable spool 90 turns in the opposite direction, such as in rewinding, the axle 78 does not experience a braking torque.

On the side of the cable spool 90 opposite that of the first pulley plate 86 is a second pulley plate 98, which is mounted on bearings so as to be freely rotatable about a spring bracket 100. The spring bracket 100 is fixedly mounted on the upper surface 26 of the lower platform 24. An axle rotation sensor 105 is mounted within the spring bracket 100 also to the upper surface 26 of lower platform 24, and is mounted coaxially with the axle 78. The axle rotation sensor 105 serves to provide a output proportional to the rotation of axle 78, which output can be used to calculate the length of cable 52 removed from the pulley and the velocity at which the cable 52 is being pulled off of the spool.

The second pulley plate 98 is fixed to the cable spool 90 so as to define a torsion spring activity 102. A torsion spring 104 is mounted within the torsion spring cavity 102, and fixed at one end to the cable spool 90, and at the other end to the spring bracket 100. The torsion spring 104 opposes rotation of the cable spool 90 in the direction of unwinding of the cable 52. Accordingly, the torsion spring 104 causes the cable 52 to snugly rewind upon the cable spool 90 when the force exerted by the user decreases below the level of forced exerted by the torsion spring 104.

In addition to the pulley assembly 84, the cable assembly 50 also includes a spur gear 106 mounted in fixed position about the upper and 80 of the axle 78 (FIG. 4). Electromagnetic brakes 108 are mounted beneath the upper platform 10, each having mounted on its respective axis a brake spur gear 110 that operatively engages the spur gear 106. A timing belt or other similar means may be employed instead of brake spur gear 110 to operatively connect the brakes 108 to spur gear 106.

Thus, when a user pulls or lifts on the handle 58, cable 52 is pulled from the cable assembly 50, and unwound from the cable spool 52. As the cable spool 90 rotates, the ratchet 88 and ratchet pawl 96 engage to rotate the axle 78, which in turn causes the spur gear 106 to rotate in that direction. The spur gear 106 operatively engages the brake spur gears 110. If the user is pulling with sufficient force to overcome the resistance supplied by the electromagnetic brakes 108 via the brake spur gears 110, the cable spool 90 will rotate and cable 52 will unwind off the cable spool 90. The user will experience a resistance proportional to the resistance exerted by the brakes 108 via the brake spur gears 110.

A variety of braking mechanisms may be used, such as electromagnetic brake, mechanical brake, hydraulic actuator, electric motor, friction brake, pneumatic brake, or other devices. suitable for resisting rotation of the spur gear 106 during unwinding of the cable 52 from cable spool 90. In the preferred embodiment, any brake or motor is suitable provided it is controllable for providing isometric, isokinetic or isodynamic resistance.

The invention also includes a first cable angle sensor 68 (FIGS. 7-9), rotatably mounted to the lifting station 200. The first sensor 68 includes a housing 70. Preferably, the housing 70 is mounted to the cable guide assembly 56 such that the axis of the housing 70 is coincident with the point at which the cable 52 exits the rollers 57.

The sensor 68 is attached to an attachment collar 71, such that the collar 71 is free to rotate about an axis 72 of the sensor. The collar is connected to a fork 73, which includes a support 73a and a guide 73b. The guide 73b may be straight (as shown in dotted lines by outline 73c), or curved 9 as shown in dotted lines by outline 73d).

During operation, the cable 52 passes through the guide 73b, such that the fork 73b moves with the cable 52. Since the sensor 68 detects the angle of the fork 73, the sensor 68 therefore effectively provides an indication of the angle of the cable 52, i.e. an angle 74. If desired, the fork 73 may be biased against the cable 52 by spring loading. As shown in FIG. 9, the first angle sensor 68 is positioned with respect to the second rollers 57 so that the point at which the cable 52 exits the rollers 57 is largely coincident with the axis 71 of the sensor 68. When tension is placed on the cable 52, and angle 74 of the cable 52 changes, the fork 73b rotates accordingly, causing the sensor 68 to produce an electric signal representative of the angle 74. The sensor 68 is a "longitudinal" angle sensor, since it detects the angle of the cable 52 in a longitudinal direction, i.e. toward or away from the user, or "front to rear".

In a preferred embodiment, the sensor 68 comprises a Clifton type 080G2282A synchro, an optical synchronization device, a digital encoder, a potentiometer, or another suitable electrical, magnetic, or optical sensing mechanism for detecting the angle of travel of the cable 52. If a Clifton synchro is utilized, only the transmitter unit is used. The transmitter incorporates an excited rotor coil, which induces voltages into a delta-wound stator field 120° out of phase with the others. Normally these voltages are transferred to a receiver wherein the rotor of the receiver tends to stay synchronized with that of the transmitters. However, in the current application, one output (not shown) of the transmitter is used as a reference (ground), resulting in two outputs whose magnitudes can be treated as rectangular coordinates for the purposes of determining the rotor position. This may be performed with a voltage divider network, analog to digital conversion, and calculation for the relative position of the rotor via a computer. The primary benefit of using common synchros is that the angle provided by the sensor 68 is substantially free from voltage fluctuations and common noise.

The invention may advantageously utilize a second angle sensor 69 (FIG. 10) to determine the angle of the cable 52 in a direction perpendicular to that detected by the first angle sensor 68. The second angle sensor 69 may be constructed of identical components as the first angle sensor 68, e.g. housing 75, attachment collar 76, fork 77, etc. When the first and second angle sensor 68, 69 are utilized together, it is preferred that the forks 73b and 77 are curved, so that the fork 73b may freely pass over the fork 77 when the user exercises.

When tension is placed on the cable 52, and the angle of the cable 52 perpendicular to the angle 74 changes, the fork 77 rotates accordingly, causing the sensor 69 to produce an electric signal representative of this angle. The sensor 69 is a "lateral" angle sensor, since it detects the angle of the cable 52 in a lateral direction, i.e. side to side with respect to the user.

In the preferred embodiment, the invention also includes a computing station 300 (FIG. 1). The computing station 300 includes a central processing unit 302 having an interface (not shown) for a permanent storage medium, such as a diskette, tape, or other similar medium. The computing station 300 additionally includes a monitor 306, a keyboard 308, and a printer 310, each being electrically attached to the processing unit 302. The force sensors 36, brakes 108, first angle sensor 68, second angle sensor 69, and axle rotation sensor 105 are electrically connected to the computing station 300 via a cable 330.

Additional data can be supplied to the computing station 300 by a tri-axial lumbar goniometer 350, which functions to measure isolated spinal lumbar motion such as rotation, flexion-extension, and lateral flexion, during the lifting exercise. An example of a suitable goniometer 350 is the Dynavec LVD brand lumbar systems, sold by Triaxial Systems of Moscow, Id. The goniometer 350 is directly attached to the patient and is electrically attached to the computing station 300 via a cable 351.

Supplemental biomechanical modeling information may also be obtained using digital imaging equipment, such as cameras 410 and 412, which are each mounted on tripods 414, and connected to the computing station 300 via cables 416–418. The cameras 410 and 412 are oriented to capture a front view and a side view of the lifting station 200 and a user upon it.

Having now described that hardware components and interconnections of the present invention, the operation of the invention will be described with reference to FIGS. 1-10. The present invention is used in analyzing a patient's body during one or more lifting operations and evaluating musculoskeletal problems of the patient. The invention is especially useful in identifying lifting-related injuries of a person that performs such operations during the regular course of his/her occupation. For ease of understanding, the invention will be described in the context of the analysis of an occupational lifting-related injury, although the usefulness of the invention is not so limited.

In a typical testing session utilizing the present invention, the first step requires the operator (not shown) of the apparatus to select the level and type of resistance desired. This resistance will be provided to the patient (not shown) by the brakes 108. This step is performed by entering the data into the computing station 300. Accordingly, the computing station 300 then passes the appropriate instructions to the brake control means (not shown), which adjusts the brake 108 to provide the desired resistance.

The patient then steps onto the upper platform 10, positioning each foot on one of the footplates 42. The patient then grasps the handle 58 lifts it one or more times in the same manner that the patient usually lifts objects in the course of his/her occupation.

During this lifting operation, a variety of data is accumulated. First, the force sensors 36 can be used to detect the patient's anterior, posterior, and lateral weight distribution pattern. The information obtained is transmitted to the computing station 300 via the cable 330.

In the preferred embodiment of the invention, the force sensors 36 are calibrated before each use or series of uses, by placing a known weight on the footplates 42, and measuring the output of the force sensors 36 in response to that force. This measurement can then be used by the computer to adjust, if necessary, the calculation of the actual force being applied on a particular sensor 36 during exercise or testing from the electrical output of the sensor 36. However, by calculating the total force applied by the user to the sensors 36 and subtracting the user's weight, the computing station 300 can determine the amount of force exerted by the user against the cable 52.

In addition to the weight distribution data, the computer also receives input from the axle rotation sensor 105, which provides information suitable for determining the length of the cable 52 dispensed from the cable spool 90 during each of the patient's exercise repetitions. In addition, the axle rotation sensor 105, together with computing station 300, provides information suitable for determining the speed at which the cable 52 is withdrawn from the cable spool 90. This length and speed data is transmitted to the computing station 300 via the cable 330.

During the lifting exercises the angle sensors 68, 69 also provides position data. In particular, the angle sensors 68, 69 determine the longitudinal and lateral angles at which the cable 52 is pulled by the user throughout the exercise session. As described hereinbelow, this map is utilized in generating a model of the patient during the lifting exercise.

If desired, limb segments of the patient may be marked with a color that may be easily detected and coded by the cameras 410 and 412, to facilitate permit the cameras 410, 412 to capture sequential video images of the user during the exercise. The computing station 300 may digitize the video images of the user exercising, isolate the movements of the colored areas, and create a biomechanical model of the user exercise.

In addition, data taken during exercise against isokinetic resistance enables the computing station 300 to determine the maximum and minimum torques that the patient can generate throughout the different positions of a lifting operation. This data can be compared with National Institute for Occupational Safety and Health (NIOSH) predictive values in order to determine the amount of weight a person can safely handle for both maximal and repetitive lifting tasks. By selecting the isodynamic mode of resistance, the lifting station 300 can be made to more closely duplicate real lifting conditions under the force of gravity. Furthermore, by programming computing station 300 to control the brake 108 to simulate the amount of weight determined to be safe for repetitive tasks, the computing station 300 can evaluate the patient's performance under repetitive, endurance-type exercises. Thus, by conducting an analysis of the patient's lifting endurance, the computing station 300 is able to measure and document the changing contribution of the weight distributions that reflect the patient's muscular recruitment pattern (i.e., with the onset of fatigue), and thereby more accurately measure safe lifting limits.

The present invention provides a number of advantages to its users. For example, in contrast with prior systems, the invention includes a computer-controlled brake 108 which is capable of selectively supplying isometric, isodynamic, and isokinetic resistance.

Another benefit of the invention is that, unlike the prior arrangements, the invention utilizes the force sensors 36 which enable the invention to provide a real-time record of a patient's weight distribution during various lifting exercises.

The invention is also beneficial since it is capable of generating a biomechanical model of the user. Specifically, the sequential encoded video images, the weight distribution data, the map of the location of the handle 58, and the lumbar measurements all provide the computing station 300 with sufficient statistical input for generation of a bio-mechanical model of the user, including the musculoskeletal leverages, forces, and torques experienced by the patient's joints and limbs during the lift. The invention is additionally capable of measuring the patient's strength.

Furthermore, the computing station 300 is able to determine the compression of the spine throughout the lifting motions, which is useful in determining the limits within which the patient can safely lift objects. Another advantages of the invention is that, in contrast to other systems, it provides input sufficient to calculate dynamic spinal pressure curves.

Still another benefit of the present invention is that the invention enables a musculoskeletal model of an exercising person to be generated, based on physiological conditions and other data such as the person's posture, the position of the person's limb segments, the position of the weight lifted by the patient, and the like.

The sensors 68, 69, and 105 provide another benefit of the invention, by measuring lift capacity and position, and permitting feedback control of the lifting exercise. Additional information concerning the patient's position during lifting can be derived form the goniometer 350.

While there have been shown what are presently considered to be preferred embodiments of the invention, it will be apparent to those skilled in the art that various changes and modifications can be made herein without departing from the scope of the invention as defined by the appended claims. For example, the braking mechanism and cable spool can be arranged in a variety of configurations and orientations.

What is claimed is:

1. An apparatus for providing resistance to the exertion of force by a human subject during exercise or physiological testing, comprising:
   a platform with a longitudinal axis and a lateral axis including two support surfaces spaced apart along the lateral axis, each support surface corresponding to one of the subject's feet;
   a length of cable and a handle attached to an end of the cable;
   a cable assembly to dispense and rewind the cable for the subject to pull while the subject is feet are on the respective support surfaces;
   a brake operatively engaged with said cable assembly for providing a controllable variable resistance to the subject's pull on the cable;
   force sensors to provide signals representative of the force exerted by the toe region, heel region, inner region, and outer region of each of the subject's feed upon its respective support surface; and
   a first angle sensor for providing output from which a lateral angle of the cable with respect to the platform may be determined.

2. The apparatus of claim 1, further comprising a rotation sensor for providing output from which the length of cable being dispensed can be determined.

3. The apparatus of claim 1, further comprising a computing station operatively connected to said force sensors and first angle sensor for assessing physiological characteristics of the subject during exercise.

4. The apparatus of claim 1, wherein the first angle sensor comprising:
   a housing having an axis;
   a fork rotatably connected to the housing so as to freely rotate about the axis; and
   a sensing device operatively coupled to the fork and the housing, for providing a signal representative of the angular position of the fork with respect to the housing.

5. The apparatus of claim 4, further comprising a second angle sensor for providing output from which a longitudinal angle of the cable with respect to the platform may be determined.

6. The apparatus of claim 5, wherein the second angle sensor comprising:
   a housing having an axis;
   a fork rotatably connected to the housing so as to freely rotate about the axis; and
   a sensing device operatively coupled to the fork and the housing, for providing a signal representative of the angular position of the fork with respect to the housing.

7. The apparatus of claim 6, wherein the axes of the first and second angle sensors are substantially perpendicular, and the forks of the first and second angle sensors are curved to permit the forks to pivot free of each other.

8. A device as claimed in claim 3, wherein said computing station is suitable for controlling the brake to provide isometric, isotonic, isokinetic or isodynamic resistance to the subject's exertion of force on the cable.

9. A method for exercise and physiological testing of a human subject, comprising the steps of:
   (a) placing the subject on a platform having a longitudinal axis and a lateral axis, and including two support surfaces spaced apart along the lateral axis, each support surfaces corresponding to one of the subject's feet;
   (b) the subject grasping a handle attached to a cable;
   (c) dispensing, rewinding, and selectively braking the cable to facilitate exercise by the subject;
   (d) detecting forces exerted by the subject's feet upon the respective support surfaces and distinguishing between forces exerted by the toe region, heel region, inner side region, outer side region, and combinations thereof; and
   (e) detecting a lateral angle of the cable with respect to the platform.

10. The method of claim 9 further comprising the step of detecting a longitudinal angle of the cable with respect to the platform, wherein the longitudinal angle is substantially perpendicular to the lateral angle.

11. The method of claim 9 further comprising the step of detecting the velocity of the cable dispensed.

12. The method of claim 9 wherein the step of selective braking comprises providing a variable resistance to the subject's exercise.

13. The method of claim 12 wherein the variable resistance of the selective braking is controlled by a computing station.

14. The method of claim 12 wherein the variable resistance comprises isometric, isotonic, isokinetic or isodynamic resistance.

15. The method of claim 9 further comprising a step of determining the force exerted by the subject during the lifting exercise by summing the forces exerted by the subject's feet upon the support surface during the lifting exercises and subtracting the user's weight.

* * * * *